U S008073712B2

(12) United States Patent
Jacobus et al.

(10) Patent No.: US 8,073,712 B2
(45) Date of Patent: Dec. 6, 2011

(54) METHOD FOR CONSOLIDATING MEDICAL RECORDS THROUGH THE WORLD WIDE WEB

(75) Inventors: Charles J. Jacobus, Ann Arbor, MI (US); Jeffrey Braun, Ann Arbor, MI (US); Paul Cobb, Ann Arbor, MI (US)

(73) Assignee: Cybernet Systems Corporation, Ann Arbor, MI (US)

( * ) Notice: Subject to any disclaimer, the term of this patent is extended or adjusted under 35 U.S.C. 154(b) by 2006 days.

(21) Appl. No.: 11/141,430

(22) Filed: May 31, 2005

(65) Prior Publication Data

US 2005/0209891 A1    Sep. 22, 2005

Related U.S. Application Data

(63) Continuation of application No. 09/540,062, filed on Mar. 31, 2000, now abandoned.

(60) Provisional application No. 60/127,511, filed on Apr. 2, 1999.

(51) Int. Cl.
*G06Q 50/00* (2006.01)

(52) U.S. Cl. ............................................. 705/3; 705/2
(58) Field of Classification Search .................. 705/2, 3, 705/4
See application file for complete search history.

(56) References Cited

U.S. PATENT DOCUMENTS

| | | | |
|---|---|---|---|
| 4,878,175 A | 10/1989 | Norden-Paul et al. ............. 705/2 |
| 5,319,543 A * | 6/1994 | Wilhelm .............................. 705/3 |
| 5,469,353 A | 11/1995 | Pinsky et al. .................. 382/131 |
| 5,513,101 A | 4/1996 | Pinsky et al. ....................... 705/3 |
| 5,655,084 A | 8/1997 | Pinsky et al. ...................... 705/3 |
| 5,664,109 A * | 9/1997 | Johnson et al. .................... 705/2 |
| 5,772,585 A | 6/1998 | Lavin et al. ..................... 600/300 |
| 5,778,882 A | 7/1998 | Raymond et al. ............. 128/700 |
| 5,867,821 A * | 2/1999 | Ballantyne et al. ............... 705/2 |
| 5,920,317 A | 7/1999 | McDonald ..................... 345/835 |
| 5,924,074 A | 7/1999 | Evans ............................... 705/3 |
| 5,974,124 A | 10/1999 | Schlueter, Jr. ............ 379/106.02 |
| 5,974,389 A | 10/1999 | Clark et al. ........................ 705/3 |
| 5,997,476 A | 12/1999 | Brown .......................... 600/300 |
| 6,006,191 A | 12/1999 | DiRienzo .......................... 705/2 |
| 6,032,119 A | 2/2000 | Brown et al. ...................... 705/2 |
| 6,032,120 A | 2/2000 | Rock et al. ........................ 705/2 |
| 6,073,106 A | 6/2000 | Rozen et al. ....................... 705/3 |
| 6,125,350 A | 9/2000 | Dirbas .............................. 705/2 |
| 6,157,914 A | 12/2000 | Seto et al. ......................... 705/3 |
| 6,199,073 B1 | 3/2001 | Peairs et al. .................. 707/204 |
| 6,260,021 B1 * | 7/2001 | Wong et al. ....................... 705/2 |
| 6,272,470 B1 | 8/2001 | Teshima ............................ 705/3 |
| 6,283,761 B1 | 9/2001 | Joao ............................. 434/236 |
| 6,408,330 B1 | 6/2002 | DeLaHuerga ................ 709/217 |

* cited by examiner

*Primary Examiner* — Gerald J. O'Connor
*Assistant Examiner* — Hiep V Nguyen
(74) *Attorney, Agent, or Firm* — Gifford, Krass, Sprinkle, Anderson & Citkowski, P.C.

(57) ABSTRACT

Medical records, clinical observations, and medical imagery are organized and aggregated into a common database, enabling the data to be viewed and/or updated by medical practitioners world-wide. The information may also be viewed and monitored by patients or their relatives for accuracy, also regardless of their location. The invention further allows the records to be updated by manually controlled or automated instrumentation which measures medical parameters whether located in a doctors office, in a hospital setting, in the patient's home, or worn by the patient. Common access and point-to-point data transmission is via the global grid, or over public access common data networks supporting TCP/IP, most often referred to as the Internet. The same approach can be using insider an organization over an internal network or Intranet.

12 Claims, 10 Drawing Sheets

METHOD FOR CONSOLIDATING MEDICAL RECORDS THROUGH THE WORLD WIDE WEB

REFERENCE TO PRIOR APPLICATIONS

This application claims priority of U.S. provisional application Ser. No. 60/127,511 filed Apr. 2, 1999, the entire contents of which are incorporated herein by reference.

FIELD OF THE INVENTION

This invention relates generally to the management of medical/dental patient records and, in particular, to a method for storing and accessing such records through the world wide web.

BACKGROUND OF THE INVENTION

Medical records are currently prepared and stored by hand in physical files, by machine and converted to physical form through print outs for storage in physical files, or by machine and stored in digital form. The typical arrangement is to use all of these means in a complex mixture within a medical facility.

The normal evolution of digital medical record preparation and storage has been within a particular doctor's practice, clinic or hospital facilities grouping. With the advent of managed care networks, proprietary systems for providing network access to the data have been built, however, no large area, multi-institution, national or international medical repository has yet been built.

There are several reasons for the lack of a centralized database. First is the importance of maintaining the privacy of data. It is also difficult to exchange data between proprietary systems which code the same types of data differently. Another problem arises from the fact that different medical establishments store some data in digital exchangeable form and other data in less portable forms (paper and film); there is currently no universal agreement as to which data is stored in what form.

Medical establishments also gain a high degree of proprietary ownership of the patient when they retain the patient's medical information, even through they typically exchange data with each other when specifically requested to do so by the patient.

The primary efforts to implement a universal standard for medical data exchange have been driven by standards organizations. One example is the Andover Group, a non-profit organization which was originally organized by Hewlett Packard, but has since been joined by several hundred other organizations and companies. Andover Group has not defined standards for interoperation, but rather has endorsed existing standards. These are principally DICOM, an ISO standard for encoding medical image data, IEEE 1073, a networking and protocol standard for collecting and transmitting clinical observation data (such as from EKG or vital signs instruments), and HL7, an encoding method for patient medical records which include billings data and chart data.

Another example is the IEEE 1073 standards organization, which is organized to define an IEEE standard for networking and protocols for collecting and transmitting clinical observation data (such as from EKG or vital signs instruments). This group was formed in 1985 when many efforts to define application-specific alternatives to IEEE 802.3, or Ethernet, were prevalent. The 1073 committee took this route in the medical field, citing that normal Ethernet did not deliver predictable data delivery timing (because it uses collision detect multiple access to media allocation), and did not provide proper interconnect for use in the medical field (which included instrument isolation, quick connect, disconnect, and star configuration wiring). The 1073 committee has successfully defined 1073.1, the interconnect technology standard, but has to date failed to complete 1073.2 and up, which define standard protocols and encodings for clinical instrument data streams. Unfortunately, in 1999, Ethernet variations no longer have the cited interconnect limitations cited in 1985, which puts into doubt the value of 1073.1. Ethernet, in the 10 and 100 baseT configurations, allows quick connect/disconnect from star networks emanating from standard hubs (which are interconnects at the phone closet); wireless Ethernet adapters allow connections to local routers without any connection; and by using routers and gateways to connect instrument, room level, or unit level subnetworks, any degree of desired data delivery latency can be achieved. As it stands, 1073.1 may never gain widespread acceptance.

DICOM is an ISO standard which was defined to allow encoding and exchange of X-ray, CAT, and other digital image format data easily. Unfortunately, much medical imagery is still stored primarily on film, which must be physically copied and exchanged. Until the common X-ray machine is fully digital, this will remain the case.

HL7 is tagged object encoding formatted, defined for medical institutions to exchange medical records between dissimilar central computer systems. HL7 is gaining widespread acceptance as the main way for hospitals to exchange their data without paper files as the intermediary. This acceptance does not yet represent a majority of institutions. As indicated in the next paragraph, HL7 is by no means the only standard being considered.

CORBA, or Common Object Request Brokering Application, is a method defined and maintained by the Object Management Group (OMG). OMG acts as a clearing house for organizations building object oriented interoperable software/systems applications. OMG organizes standards committees much like the IEEE, ANSI, or ISO, but centered around object oriented programming methodology. CORBA is OMG's framework for all of these standards activities. Within the CORBA umbrella is the CORBAmed group. CORBAmed is focused on defining interoperable medical applications and standards which leverage the basic CORBA object oriented messaging and coding approach. CORBAmed has units which are concerned with defining interoperability with HL7 (and actually coding versions of HL7) within CORBA. CORBAmed is also currently defining Clinical Observation and Analysis Systems (COAS) using COBRA methods. Thus CORBAmed is very much a counter point to the Andover Group, IEEE 1073, and HL7. A similar effort at Microsoft to leverage COM, an alternative common object model has begun to address medical data management applications.

U.S. Pat. No. 5,778,882 to Raymond describes a system which tracks the health status of a patient by compiling a chronological multi-parameter health history from multiple sensors in contact with the patient's body. However, this system does not explain how the data is integrated with other types (for instance, image data or written patient record data such as billings or diagnosis events) or how the data is retained from previous procedures performed. Thus, this system misses the patient's whole life data recording, archival, and retrieval function.

U.S. Pat. No. 5,924,074 to Evans shows how text-type patient record data can be created and maintained electronically. This information includes complaints, lab orders, medications, diagnoses, and procedure descriptions. The description is of a specific implementation which appears to map directly on the structure described by documents associated with the definition of HL7, the standard for hospital and medical data record exchange. The key patented innovation is using pen-based portable computer interfaces. In this patent, we focus on presentation, data capture, and data integration for long term archival and retrieval. If the user prefers a portable user interface, a pen-portable computer would be appropriate, however, normal web-data terminal interfaces are usable as well.

U.S. Pat. No. 5,974,124 to Schlueter describes a system which assists doctors in treating patients with long term medical conditions. The system includes storage of medical data taken from the patient's body, presentable through the world wide web, however, does not address methods for dealing with multiple data types, protocols, or interfaces, and does not show how to incorporate paper based records. In addition, record keeping does not describe how the data will be maintained over the entire life of a patient.

U.S. Pat. No. 5,997,476 to Brown describes remote data collection, both in question answer form and data measurement form, for the purposes of transmission to the clinician and for subsequent display. This patent, however, does not describe how protocol, multiple data formats, and data archival are integrated together.

U.S. Pat. No. 6,032,119 to Brown describes display of individualized patient health status on a HTML display which depicts the human body. This is an interesting display method, but is limited to the specific integration of data required for the display coupled to its representation format. It does not describe archival or data collection specifically.

None of these standards efforts have addressed combining all medical data into a common database accessible or updateable from anywhere by anyone with appropriate access rights. Current methods do not teach how all forms of medical data from all sources are read in initially and updated routinely, nor do they explain how all forms of medical data from all sources are viewed and/or updated manually by patients, doctors, or other medical staff.

SUMMARY OF THE INVENTION

This invention defines a method for aggregating medical records, clinical observations, and medical imagery into a common database. This enables the data to be viewed and/or updated by medical practitioners regardless of their location world wide. The information may also be viewed and monitored by patients or their relatives for accuracy regardless of their location. The method further allows the records to be updated by manually controlled or automated instrumentation which measures medical parameters whether located in a doctors office, in a hospital setting, in the patient's home, or worn by the patient. Common access and point-to-point data transmission is via the global grid, or over public access common data networks supporting TCP/IP, most often referred to as the Internet. The same approach can be using insider an organization over an internal network or Intranet.

BRIEF DESCRIPTION OF THE INVENTION

DETAILED DESCRIPTION OF THE INVENTION

This invention takes advantage of the fact that a number of the critical elements required to make a fully integrated medical information resource are already available. This invention combines these elements into an innovative information access/management system which may be assessed via the World Wide Web.

The requirements include:

1) Defined common formats for all relevant medical data objects;

2) A world wide digital data interconnection infrastructure;

3) Computer-based data management systems large enough and fast enough for the amount of data likely to be stored;

4) A universal data interface model which will allow all types of data viewing clients to review said data;

5) A method for acquiring medical data from instruments, imaging systems, medical record keeping systems, and manual (paper-based) records; and 6) A method for motivating institutions and individuals to present said data to the central archival authority.

Beginning with 6) above, a fundamental reason for migration to a common medical data archival system is that each individual covered is unique, and therefore has a unique medical record track. As individuals move from place to place world wide, their medical records need to move instantaneously with them. Each observation or procedure which the individual undergoes must be referenced to his or her prior medical history and must be added to this history for reference in the future. It has been proposed that this could be done through smart cards or some other portable data storage media, but in fact, to represent even a small amount of the data developed on the individual within a small data space is not feasible. Within a central data archival system (which may be implemented as multiple computers operating logically together to appear as a unified system) storing the relevant data is very feasible. By providing access to this data via the World Wide Web, access to the data from anywhere on any data terminal becomes feasible.

Thus, the individual is motivated to have has or her medical records centrally stored and accessible (assuming adequate security measure are taken so that the records cannot be improperly used, for instance, by the Government or insurance carriers). As with the legal profession, in the medical profession, it is assumed that the data from the individual is owned by that individual, and can therefore, by individual directive, be transferred among medical practitioners or researchers with the approval of said individual.

Figure 1:
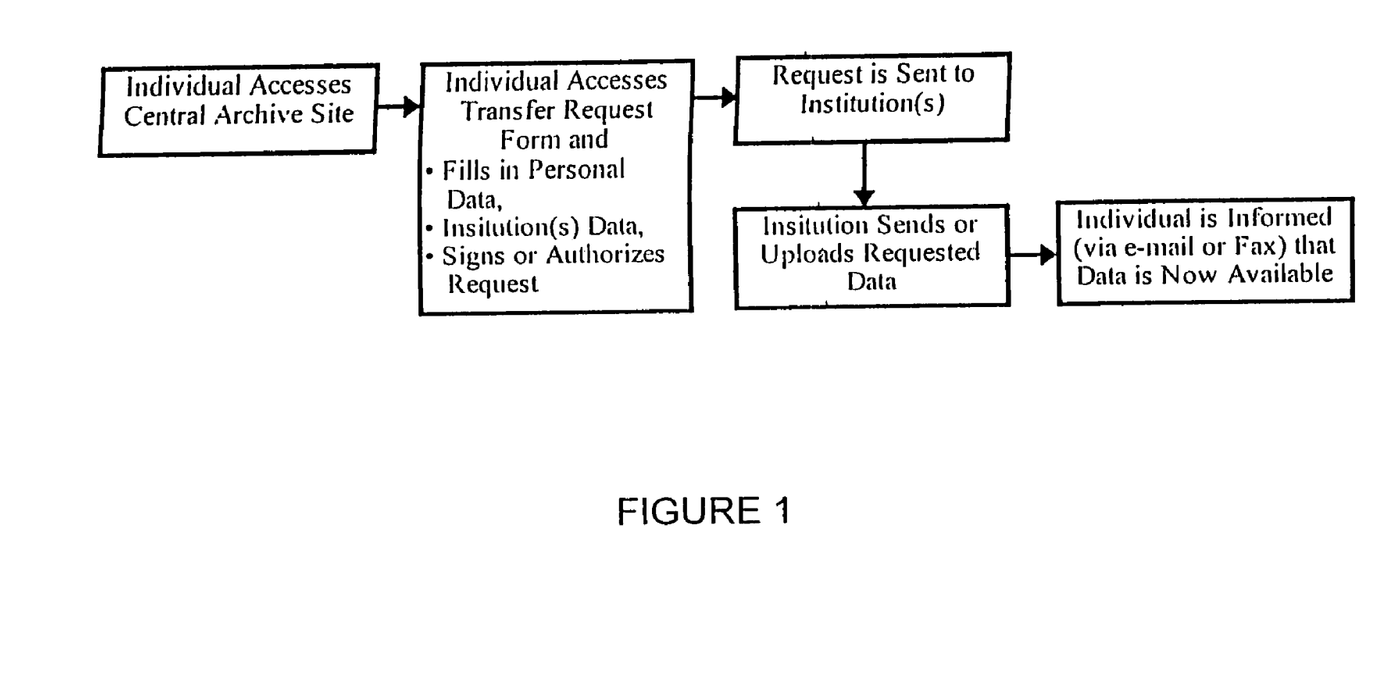
FIG. 1 is a diagram which shows how medical records may be transferred from institutions to a central archival system according to the invention.

Thus, the medical practitioner or institution can be motivated to upload or provide an individual's records simply by being formally requested to so by the individual. In the invention there will be a form or document (presented by the central web site in electronic form or alternative paper-based form) which the individual patient can authorize the central archival authority to acquire his or her medical records from the designated medical institutions. As shown in FIG. 1, these records will then be transferred from said institutions to the central archival systems (with whatever recoding of the data is necessary for central archival and viewing).

This transfer method from medical institutions, referred to as 5), will take at least four forms:
 a) transfer from online medical records;
 b) transfer from online instruments and/or image sources;
 c) transfer from offline films;
 d) transfer from offline paper documents.

Figure 2:
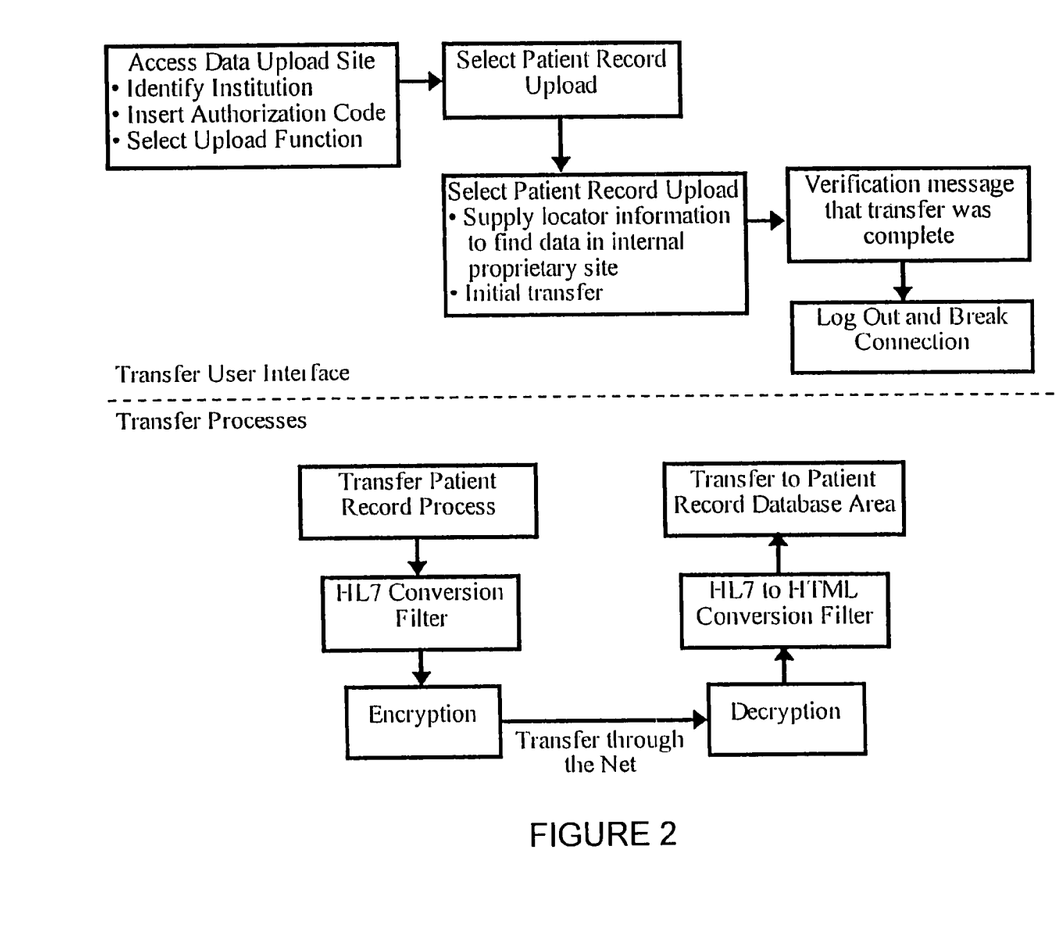
FIG. 2 is a diagram which shows how an archival site according to the invention provides an interface allowing a medical institution to export data.

A central medical archival system according to the invention presents a common interface to medical institutions which allows viewing of medical data (to be described later), and which allows convenient uploading or updating of data. This interface consists of standard methods for handling all the types of interactions (a)-(d) indicated above. For transfer of online medical records (a) the archival site will provide an interface which allows the medical institution to export data in HL7 format from its proprietary internal formats, as shown in FIG. 2.

Figure 3:
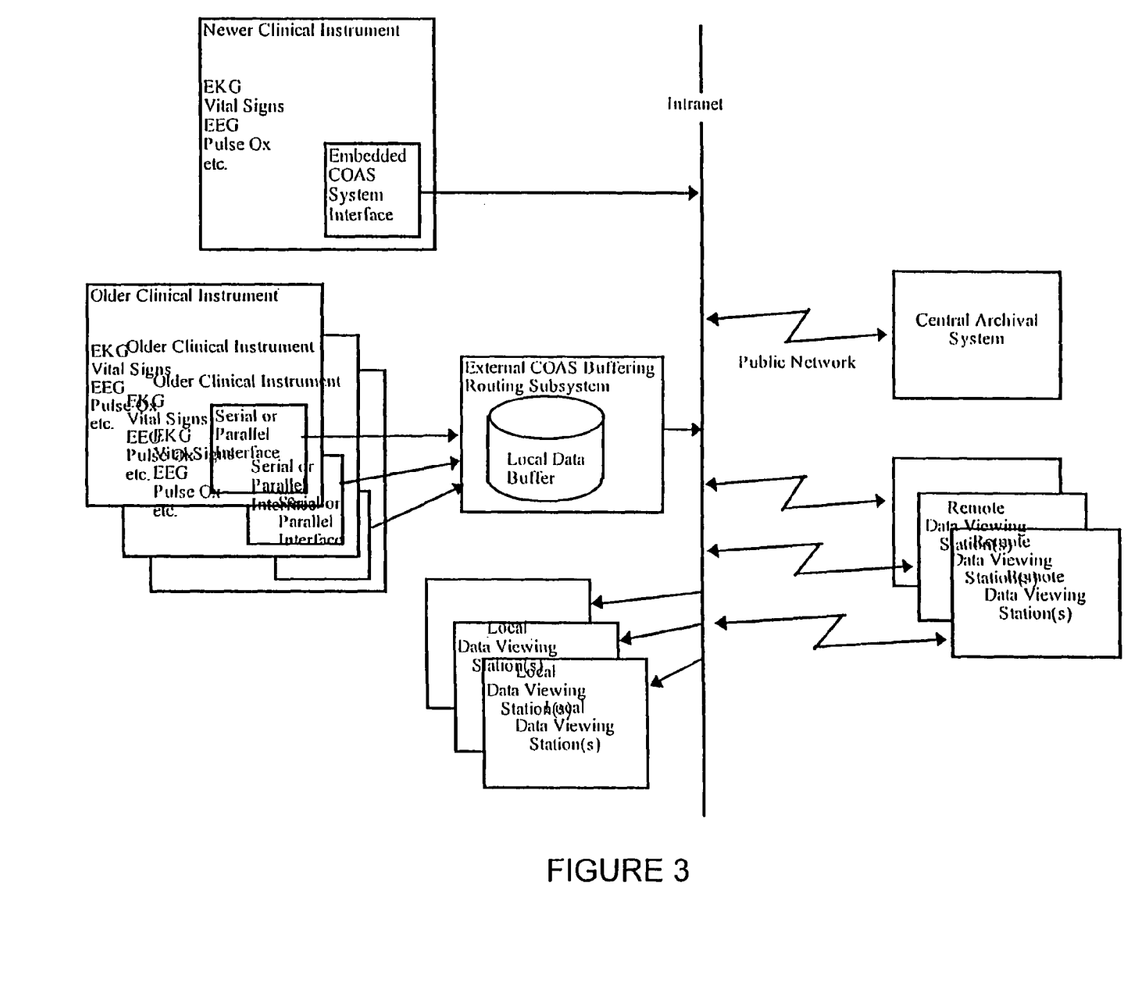
FIG. 3 shows how a clinical observation and analysis system (COAS) is used to collect and format data.

For instruments which allow for export of data (b), a Clinical Observation and Analysis System or COAS will be used to collect and format data, as shown in FIG. 3. It is expected that modern instruments will embed the COAS interface within the instrument, while older instruments may connect to an external data encoder/router. After data is encoded it will flow to a central data archival system through the Intra or Internet following whatever network topology is in place. Any link may be wired, optical or wireless as long as it is logically connecting in the global grid or the combined public net sometimes referred to as the Internet. Each stop along the route may or may not contain an internal buffer store to hold data for redundancy, further processing, or to accommodate data flow through delays or temporary stoppages. Such system is described by Cybernet Systems Corporation's Data Collection and Analysis Environment (DCAE), by the CORBAmed COAS, or by the applications layer documents for IEEE 1073, the entire contents of each of which is incorporated herein by reference.

Figure 4:
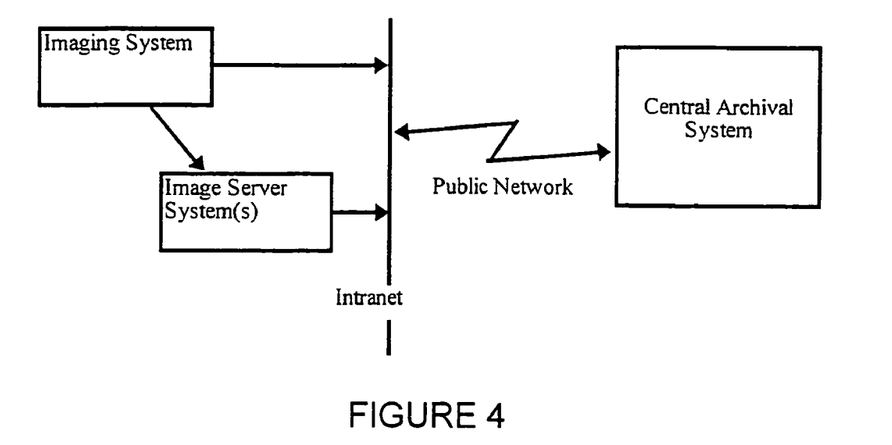
FIG. 4 is a diagram which shows how image data is stored on-line in a distributed file system.

For imaging systems which allow for export of data (b), an image encoding and transfer method will be used, as shown in FIG. 4. The preferred approach is to use industry standard image formats such as GEF, TIFF, JPEG, or others or DICOM, the most commonly used medical image standard. As indicated in FIG. 4, image data is typically stored online in a distributed file system, which may be separated from the actual imaging system. In either case, for online medical data, images or observation data, an interfacing system installed in the medical establishment will make the connection from internal data system to the central archival system over the Internet.

Figure 5:
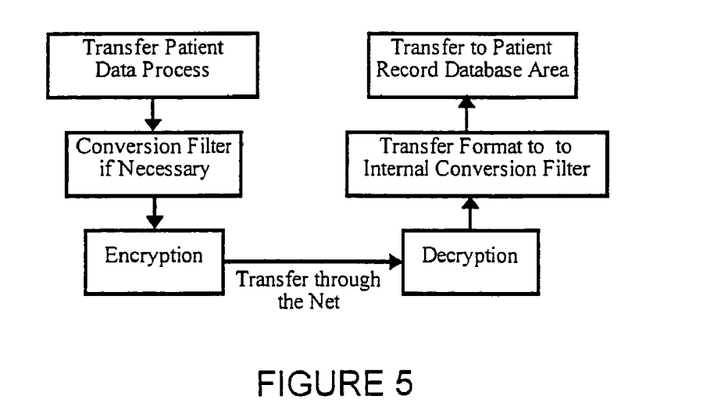
FIG. 5 is a diagram which shows how patient data may be encrypted and filtered for transfer to a patient record database area.

The inventive system will also decode proprietary data, encrypt it for transfer of public carriers, and at the central archive, decrypt it for storage. As shown in FIG. 5, each medical institution will be given a unique identifier and access key(s) which it will be given access to the central archival upload functions. The encryption/decryption will include a public/private key system so that the central archive can validate that the data is from the designated data source institution.

Figure 6:
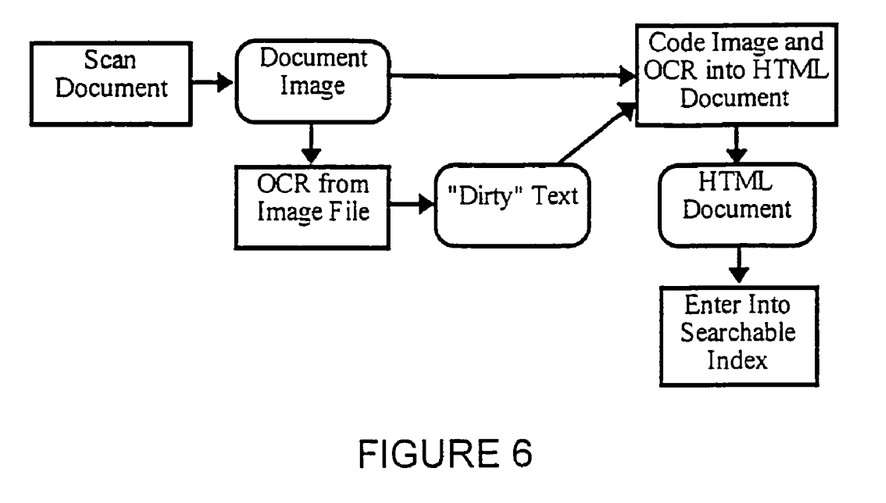
FIG. 6 is a diagram which shows how paper or film may be scanned to capture medical documents in a standard image format.
Figure 7:
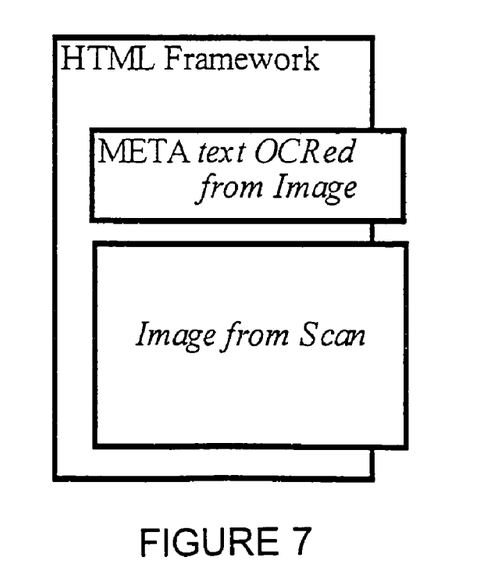
FIG. 7 is a diagram which shows how records may be coated using HTML with text being encoded using meta tags.

For transfer of offline data, either films or paper documentation, the central system will encode the data as a specialized image coded for World Wide Web review. The basic approach, shown in FIG. 6, is to scan the paper or film using a scanner or digital document capture system into a standard image format like GIF, JPEG, or DICOM. If the image includes print data, we then subject the image to automated optical character recognition, OCR. Thus, there are two types of data associated with the record: the original image and "dirty" or not-guaranteed-correct text from the OCR function. The record is then coded at an HTML document which references the scanned image and codes the "dirty" text as Meta tags (FIG. 7). With this method, no manual intervention in the image or paper upload is necessary, and the resulting record is searchable.

As indicated earlier, the user interfaces for the medical institution, physician and the patient (4) are implemented through the World Wide Web. This means that each record to be viewed will be accessible via an HTML browser on any computing platform where an HTML browser can be run. HTML allows for patient, physician, or hospital fill-in of forms, can present text, signal or image data, and can be interfaced to database and applications backend processes (via CGI). The central data resource will therefore be implemented broadly at three distinct interfaces (which can be viewed at three distinct web sites). The first is for the patient for requesting his/her medical records from specific institutions and for viewing these records. The second is for the physician or clinician for viewing patient records and for creating/update records (assuming proper authorization). The third is for the medical institution primarily for uploading records created within the institution (this interface may actually be similar to the physician interface so that records can also be reviewed).

Figure 8:
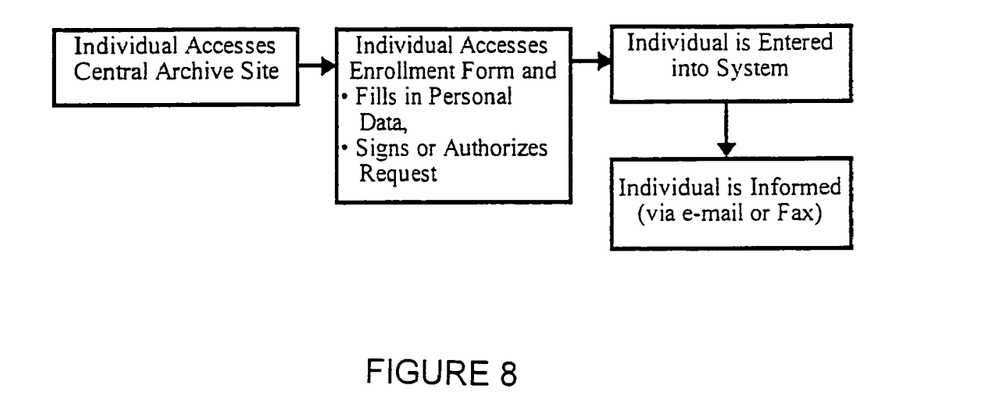
FIG. 8 shows an interface permitting patient self-registration.
Figure 9:
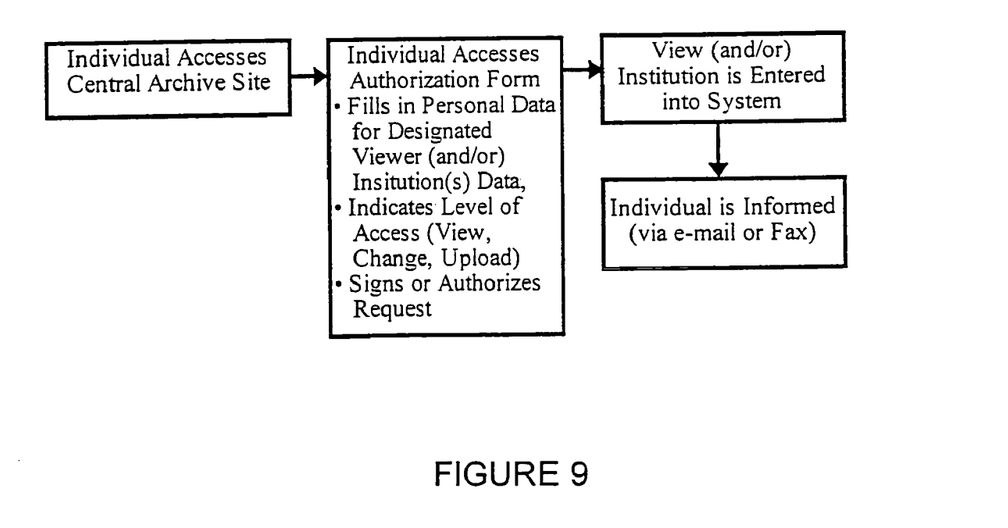
FIG. 9 is a diagram which shows how names and authorization codes may be used with respect to clinician record access for specific rights.
Figure 10:
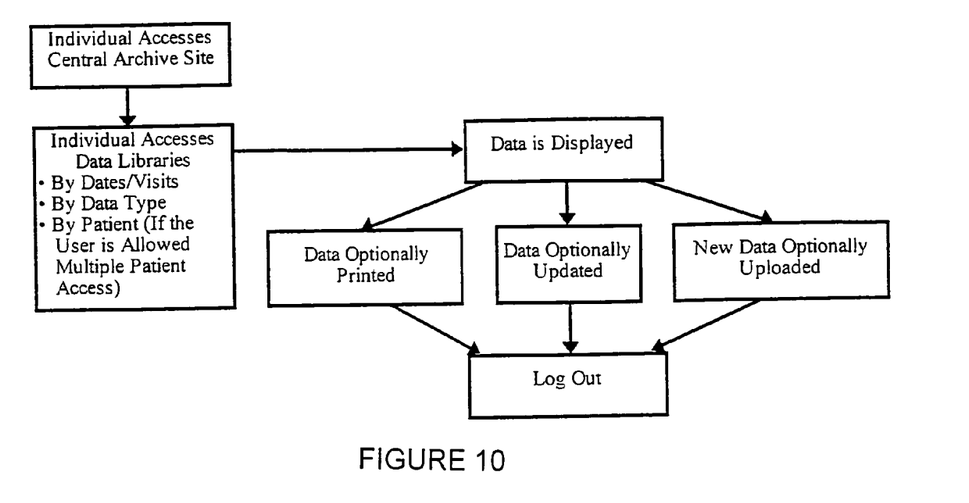
FIG. 10 is a diagram which helps to explain a self-record review process according to the invention.

The Patient Interface allows patient self-registration (FIG. 8), requests for upload of patient records from a medical institution (FIG. 1), authorization for access to medical records (where the patient indicates the names and authorization codes for clinician record access and specific access rights—FIG. 9), and self-record review (FIG. 10).

Figure 11:
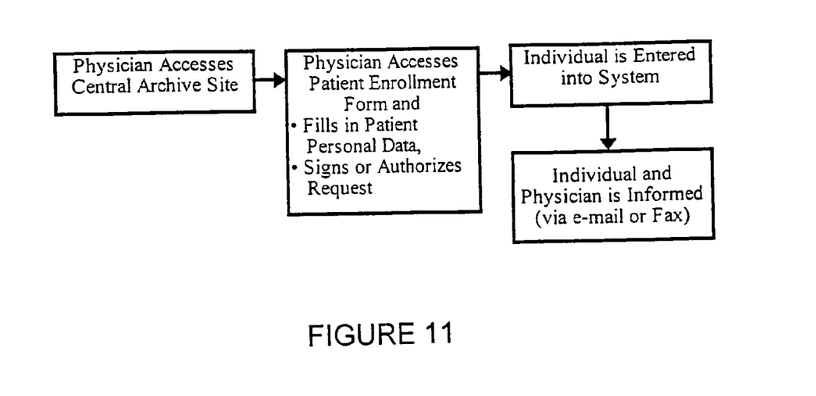
FIG. 11 is a diagram which shows how a clinician interface may be used to upload or update patient records.
Figure 13:
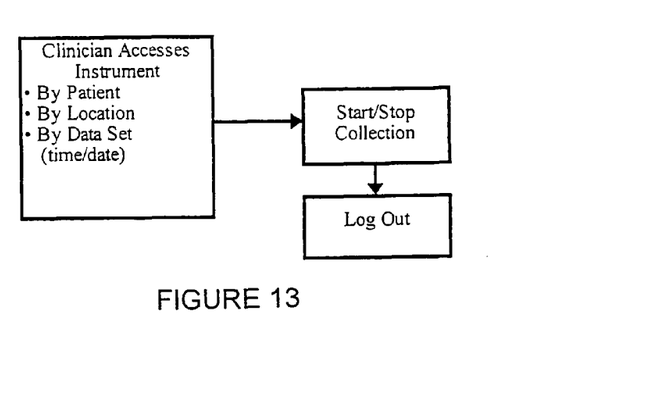
FIG. 13 shows how the institutional interface may be used to set up remote instruments.

The Clinician Interface allows the physician to register one or more of his/her patients (this is an alternative patient self-registration—FIG. 11), upload or update patient records (FIG. 11), set-up remote instruments (which monitor his/her patients and create clinical observation data—FIG. 13), and review authorized patient records, images, or clinical observation data (FIG. 10). As necessary for proper management, this interface will also provide for various summary reports per patient and in summary to keep track of online data stored in the system.

Figure 12:
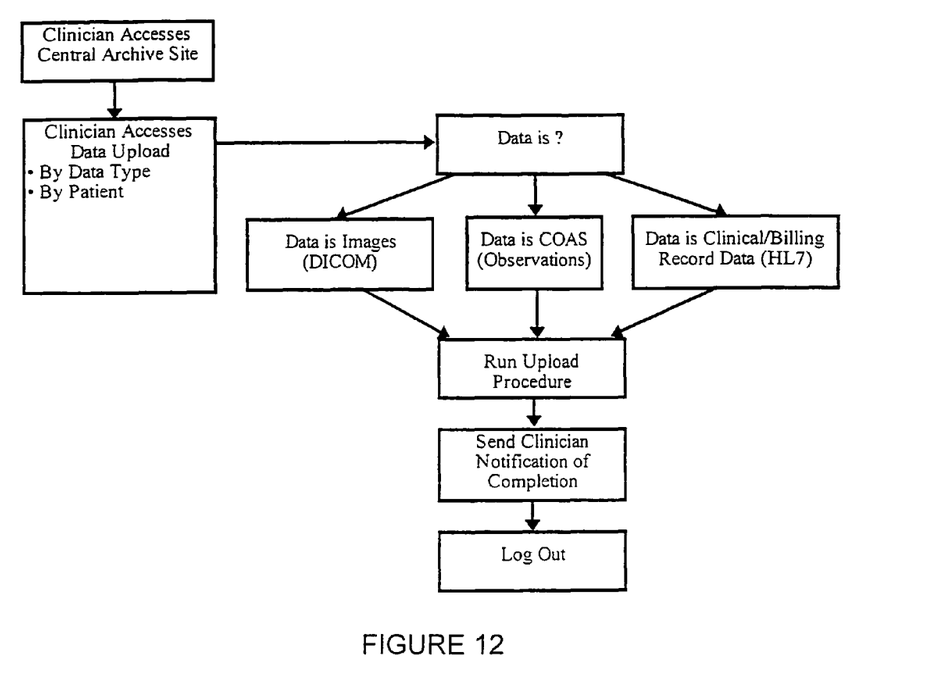
FIG. 12 is a diagram which shows how an institutional interface may be used to upload or update patient records.

The Institutional Interface allows hospital personnel to register one or more of his/her patients (this is an alternative patient self-registration—FIG. 11), upload or update patient records (FIG. 12), set-up remote instruments (which monitor his/her patients and create clinical observation data—FIG.

13), and review authorized patient records, images, or clinical observation data (FIG. 10). As necessary for proper management, this interface will also provide for various summary reports per patient and in summary to keep track of online data stored in the system.

To further define interface requirements typical to the physician, medical technician, patient, inventory control personnel, billing staff, insurance (payment for services) staff, and administrative staff, the following itemizes the typical capabilities that each staff specific user interface contains:

Physician:

| | |
|---|---|
| Email | Billing information |
| Physician-only discussion board | Help |
| Global discussion board | Log review |
| Device Tracking | Reference |
| View current patient data | Profile (Physician preferences) |
| View past (archived) patient data | Search |
| Add new patient | Logout |
| Scheduling | |

Technician:

| | |
|---|---|
| Email | Reports |
| Receive calls | Billing information |
| Technician discussion board | Log review |
| Global discussion board | Help |
| Patient information confirmation | Preferences |
| Data confirmation | Search |
| Data evaluation | Logout |

Patient:

| | |
|---|---|
| Email | Personal profile |
| Patient discussion board | Scheduling information |
| Global discussion board | Help |
| Physician instructions/diagnosis | Preferences |
| Administration instructions | Search |
| Billing information | Logout |

Inventory Control:

| | |
|---|---|
| Event Log | Log review |
| Scheduling | Billing |
| Inventory records | Help |
| Reports | Search |
| Code maintenance | Logout |

Billing:

| | |
|---|---|
| Event Log | Log review |
| Scheduling | Billing |
| Inventory records | Help |
| Reports | Search |
| Patient records | Logout |
| Code maintenance | |

Insurance:

| | |
|---|---|
| Event Log | Log review |
| Scheduling | Billing |
| Reports | Help |
| Patient records | Search |
| Code maintenance | Logout |

Administration:

| | |
|---|---|
| Email[11] | Billing information |
| Administration discussion board | View Logs |
| Global discussion board | Help |
| View schedules | Preferences |
| View online persons | Search |
| Monitor database | Logout |
| View lists | |

Figure 14:
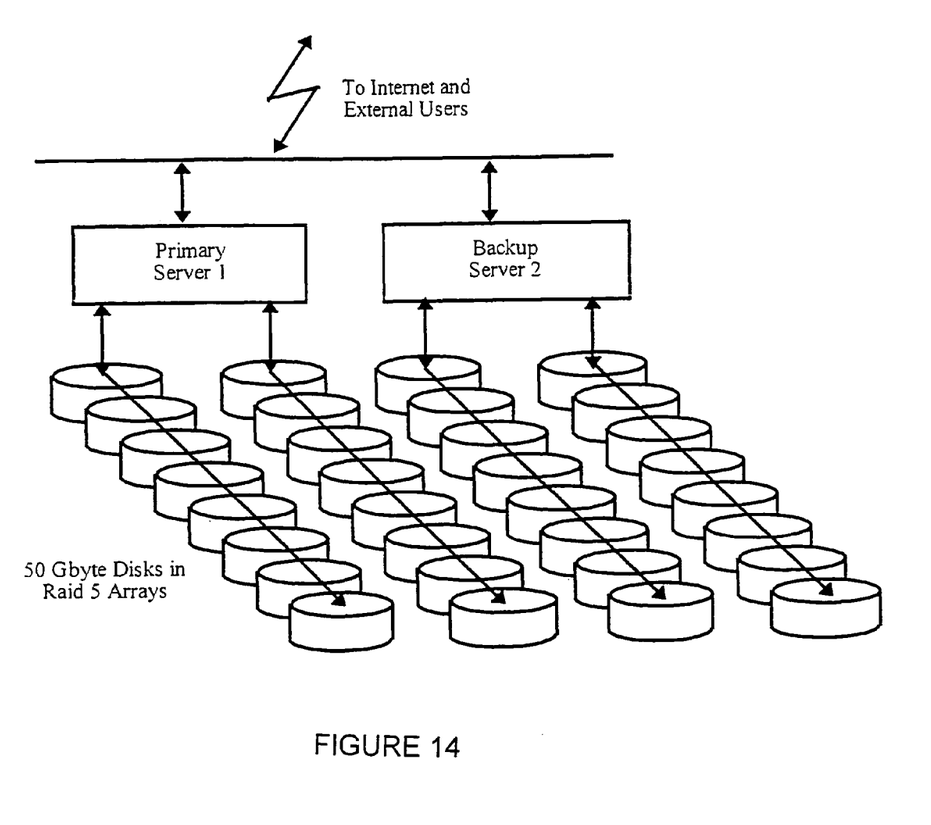
FIG. 14 is a drawing of a very large database utilizing raid arrays.

FIG. 14 shows a typical arrangement (3) capable of storing better than a terabyte in reliable form. Through the use of Raid 5, no single failure can cause data loss. Additional redundancy indicated increases failure tolerance and allows for no downtime due to failure of a single computer complex. A terabyte of memory as shown will be capable of storing records for approximately 500,000 patient lifetime records. In 1999 this system will cost approximately $50,000 or $0.10 per patient—probably less than a smart card.

This invention assumes the existence of common representational formats (1) including a standard COAS format (which can be Cybernet System's DCAE protocols and formats), a standard image format(s) which can be DICOM, GIF, TIFF, JPEG, etc., and a standard patient record encoding format which can be HL7. It also assumes the existence of a pervasive digital interconnection infrastructure with standard transport protocols and routing systems, which can be the Internet (or Intranets based on TCP/IP).

In this preferred embodiment, medical records and patient data transactions by technicians or physicians will be performed on industry standard web terminals, typically a PC, browser, and specialized real time viewing systems for images and/or other medical signals. The web interface should use the following characteristics:

Visually appealing
Simple to use interface
Provide all the functionality competitor services supply
Provide all the functionality that users (physicians) want but is not currently supplied by competitor services
Have an open-ended architecture to allow for easy future interface expansion
Provide suitable advertisement or other informational displays from the service provider to the service users space.

Figure 15:
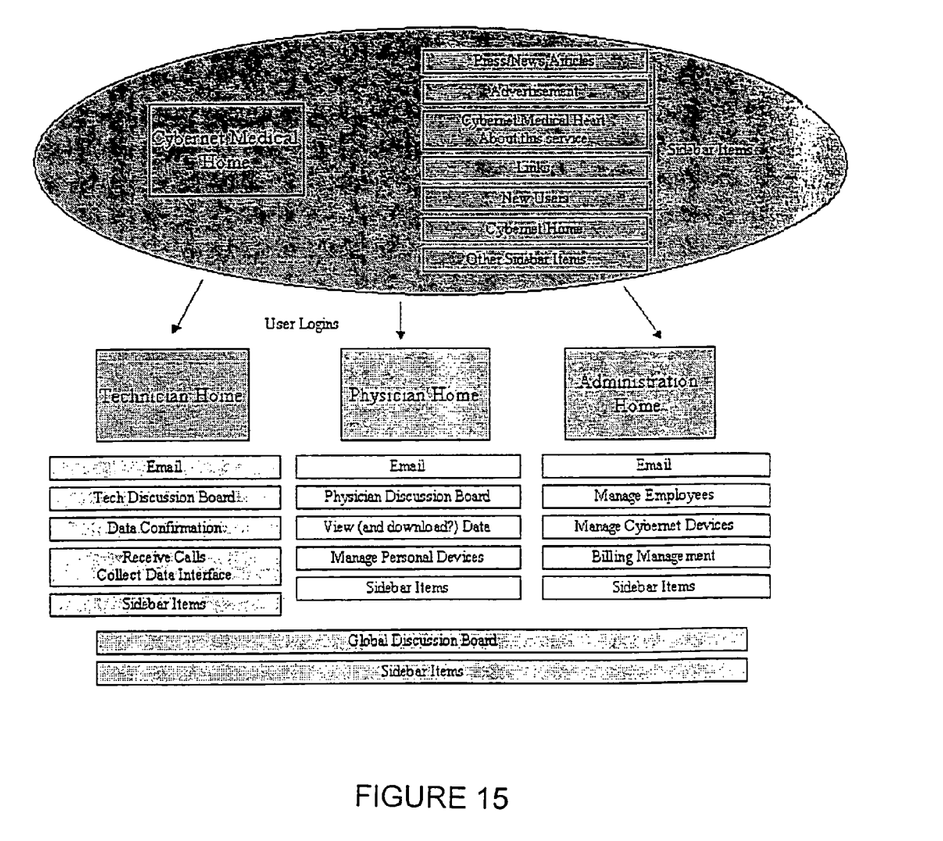
FIG. 15 represents a typical web page map of a robust system according to the invention.

FIG. 15 represents the typical web page map of the system at the highest level. There are 4 basic areas:
Site Home
Technician Pages
Physician Pages
Administration Pages Patient interface pages would preferably be structured to be subsets of the physician's page made specific to the single patient (i.e. without features to access multiple patient pages).

Details of each major section shown in FIG. 15 follow.

Cybernet Medical Home
1. Advertisement space User Login
2. General Information about the service 3. Regulatory Information
4. Sidebar Items
   a. Press and News Articles (link to the article, if online)
   b. Advertisements
   c. About the Service
      i. Features
      ii. Benefits
      iii. Operation/Process
   d. Contact Information
      i. New User Enrollment (described in separate section)
      ii. Business Partnerships
      iii. Cybernet Systems Corporation
   e. Resources/Links
      i. Medical Information Sources
      ii. Journals
      iii. Equipment Suppliers
      iv. Medical Search Engines
      v. Other
   f. Employment Opportunities
   g. Cybernet Systems Corporation Home Page New User Enrollment (Information Request)
1. Contact Names and Phone Numbers
2. Submit Information
   a. Personal Information
      i. Name
      ii. Address
      iii. Phone
      iv. Fax
      v. Pager
      vi. Email
      vii. Cell Phone
   b. Office/Business Information
      i. Address
      ii. Phone
      iii. Fax
      iv. Insurance Carrier Participation
   c. Best Time/Method to Contact
   d. Device Requirements
      i. # of devices needed
      ii. Types of devices needed
      iii. Duration devices needed
   e. Number of expected patients
   f. Specific Questions about the Service Technician Features
1. Email account and/or management tool
2. Receive Incoming Calls
   a. From Patient (the following procedure is followed)
      i. Input/confirm patient information
      ii. Record patient comments
      iii. Initiate data transfer and collection
      iv. Launch data viewing application and validate data transfer
      v. Evaluate patient data
      vi. Create report
      vii. Notify physician of event and available data
      viii. Follow-up/confirm physician receipt of report
   b. From Physician's Office (following actions may be performed)
      i. Update/confirm Physician information
      ii. Confirm that patient data has been received
      iii. Enroll new patient and create information record
      iv. Activate/deactivate patients
      v. Modify Patient Schedules
      vi. Update Device Inventory Records
      vii. Answer any questions or transfer physician to Administration
3. Technician only discussion board
4. Global discussion board
5. Patient Information confirmation (described in separate section)
6. Data Notification Confirmation (described in separate section)
7. Activity Logs
   a. Record of login/logout times and dates
   b. Record of number of calls taken
   c. Average time per call
   d. Record of number of confirmations
   e. Etc.
8. Help (on service operation and Web interface usage)
9. User Preferences
   a. View/Edit Personal Profile
   b. Set optional interface features
   c. Customize interface operation
10. Search Database
11. Logout Physician Features
1. Email account and/or management tool
2. Physician-only discussion board
3. Global discussion board
4. Device Tracking
   a. Sort by ownership, location, ID#, patient assignment, etc.
   b. Update device location/status database (for devices under their control)
5. View/manage patient information
   a. Update patient information (see separate section)
   b. Update patient status
      i. Active/inactive
      ii. Current procedure(s) prescribed
      iii. Device assignment(s)
      iv. Other
   c. Notify service about status change
6. View list of active patients and select specific patient data set for viewing
   a. Launch viewing application and display data (viewing application is discussed in separate section)
   b. Display summary report
   c. Add Comments and Expert Diagnosis to the report
   d. Generate hardcopy printouts of report and/or raw data
7. View Archived patient data
   a. Same functions as for active patient data
8. Enroll New Patient in the service
9. Help (on the service operation and the Web interface)
12. User Preferences
   a. View/Edit Personal Profile
      i. Full Name
      ii. Personal
         1. Email
         2. Pager #
         3. Cell Phone
         4. Home Address
         5. Home Phone #
      iii. Office
         1. Office Address
         2. Office Phone and Fax
         3. Insurance Carrier Participation
      iv. Notification Preferences
         1. Email
         2. Email hyperlinks to the data and report
         3. Phone
         4. Fax
         5. Pager
         6. US Mail (for hardcopy followup)

b. Set optional interface features
c. Customize interface operation
10. Search Database
11. Logout Administration Features
1. Email account and/or management tool
2. Administration-only discussion board
3. Global discussion board
4. View Schedules
   a. Number of calls expected per day
   b. Number of technicians working and/or expected to work today, and what hours each technician can be expected.
2. View users currently online
3. View device inventory
   a. Device number and type
   b. Doctor assigned to
   c. Patient assigned to
   d. Date assigned
   e. Date expected back
   f. Status
4. View Lists
   a. Physicians
      i. Personal data
      ii. Usage History
         1. Average # of notifications needed per event
         2. Payment history
         3. Average # of notifications needed for device returns
      iii. Enrolled Patients
      iv. Insurance Participation
   b. Patients
      i. Personal data (See Patient Information Section)
      ii. Event and Transaction logs
   c. Insurance
      i. Participating Doctors
      ii. Enrolled Patients
5. Billing Information
   a. Payment Status
   b. Overdue Billing Follow-up
6. Help (on service operation and Web interface)
7. User Preferences
   d. View/Edit Personal Profile
   e. Set optional interface features
   f. Customize interface operation
8. Search
9. Logout Insurance Features
1. Email
2. Insurance-only discussion board
3. Global discussion board
4. View Patient/Physician accounts
5. Help
6. Preferences
7. Search
8. Logout Data Notification Confirmation This feature actively tracks all new data until receipt by the physician has been confirmed. It manages and records the date, time, and method by which physicians were notified about new patient data, as well as the date, time, and method by which the physician confirmed receipt.

The following lists and operations are available to the technician and service managers:
1. Current Data
   a. Patient Name and ID #
   b. Technician Name and ID # who received the patient data
   c. Notification Attempt History (for each attempt:)
      i. Date and Time
      ii. Technician Name and ID # who sent notification
      iii. Notification means (email, fax, voice, pager, mail)
   d. Next notification should be sent by TIME on DATE
   e. Send new notification operations
2. Past (Confirmed) Data
   a. Items listed in #1 above
   b. Date and time notification confirmed
   c. Technician Name and ID # who received confirmation
   d. Identification of who confirmation was received from Patient Information The following is displayed when an authorized user requests patient information:
1. General
   a. Patient Name and ID #
   b. Address
   c. Email
   d. Phone
   e. Pager
   f. Fax
   g. Physician (also a hypertext link to Physician's information)
   h. Insurance Carrier and ID #
   i. Billing Status
2. Medical Information
   a. Known Conditions and diagnoses
   b. Description of symptoms
   c. Medications prescribed and in use
3. Implant Devices
   a. Pacemakers
   b. Programming (current and history)
   c. Other
4. Device Tracking Information
   a. Device Type
   b. Device ID #
   c. Device Owner
   d. Date Sent Out
   e. Date Expected Back
5. Scheduling
   a. Expected call in schedule
   b. Expected doctor visits and physician follow-up
   c. Is patient up to date with schedule?
6. Event History and Statistics
   a. # of call-ins
   b. # of emergency calls
   c. # of missed check ins
   d. # of on-time check ins
   e. Payment history

We claim:

1. A method of managing patient information, comprising the steps of:
   acquiring patient information from medical instruments or imaging systems and existing medical records, including film and documents;
   storing the information on one or more computer networks associated with medical practices or institutions;
   providing one or more interfaces to a wide-area network independent from the computer networks associated with the medical practices or institutions, the interfaces allowing access to the information by the patient's physician or clinician; and wherein the interfaces further provide secure access to the information directly by the patient.

2. The method of claim 1, wherein:
the wide-area network is the internet; and
the interfaces are web browsers.

3. The method of claim 1, wherein the interface allowing access to the information by the patient permits one or more of the following operations:
self-registration by the patient,
requests for the uploading of medical records from a medical institution,
non-patient access authorization, and
review of the patient's medical record.

4. The method of claim 1, wherein the interface allowing access to the information by the patient's physician or clinician permits one or more of the following operations:
registration of one or more patients,
uploading of patient records,
remote instrumentation interfacing, and
authorized record review.

5. The method of claim 1, wherein the step of acquiring patient information from medical instruments or imaging systems uses an HL7 format.

6. The method of claim 1, wherein the step of acquiring patient information existing medical records, including film and documents uses a clinical observation and analysis system (COAS).

7. The method of claim 1, wherein the information from existing medical records is converted into a GIF, TIFF, JPEG or DICOM file.

8. The method of claim 1, wherein information from existing medical records is stored in raw and OCR versions.

9. The method of claim 1, wherein the information from medical instruments or imaging systems is contained in a GIF, TIFF, JPEG or DICOM file.

10. The method of claim 1, wherein the information from medical instruments or imaging systems is stored in raw and OCR.

11. The method of claim 1, wherein some or all of the interfaces use encryption and decryption to protect patient privacy.

12. The method of claim 11, wherein the encryption and decryption is based upon public or private key cryptography.

* * * * *